United States Patent [19]

DePompei

[11] Patent Number: 4,723,024

[45] Date of Patent: Feb. 2, 1988

[54] PREPARATION OF SILVER CARBOXYLATES

[75] Inventor: Michael F. DePompei, Mentor, Ohio

[73] Assignee: Mooney Chemicals, Inc., Cleveland, Ohio

[21] Appl. No.: 876,686

[22] Filed: Jun. 20, 1986

[51] Int. Cl.$^4$ ............................ C07F 1/10; C11C 1/00
[52] U.S. Cl. ..................................... 556/114; 260/414
[58] Field of Search ......................... 260/414; 556/114

[56] References Cited

U.S. PATENT DOCUMENTS

| | | | |
|---|---|---|---|
| 3,048,469 | 8/1962 | Brown | 556/114 X |
| 3,458,544 | 7/1969 | Bryan | 556/114 X |
| 3,887,597 | 6/1975 | Ohkubo et al. | 260/414 |
| 3,960,908 | 6/1976 | Ikenoue et al. | 260/414 |
| 4,060,535 | 11/1977 | Cinco | 556/114 X |
| 4,273,723 | 6/1981 | Hayashi et al. | 260/414 |

*Primary Examiner*—Helen M. Sneed
*Assistant Examiner*—George R. Fourson
*Attorney, Agent, or Firm*—Renner, Otto, Boisselle & Lyon

[57] ABSTRACT

The invention discloses a method of preparing a silver salt of an organic acid comprising the steps of:
(A) preparing a mixture of:
 (1) at least one organic carboxylic acid,
 (2) a hydrocarbon solvent, and
 (3) a mineral acid; and
(B) adding a source of silver cation while maintaining the temperature of the resultant mixture between about 60° C. and below the decomposition temperature of the components and product for a period of time sufficient to form the desired silver salt.

24 Claims, No Drawings

PREPARATION OF SILVER CARBOXYLATES

TECHNICAL FIELD

The present invention relates to an improved method for preparation of silver carboxylates.

BACKGROUND OF THE INVENTION

Many types and mixtures of metal salts and soaps of natural or synthetic organic acids, particularly carboxylic acids, have been suggested and commercially offered over several decades. These have been used to supply metals in forms which are soluble in organic liquids, especially in various hydrocarbon oils and solvents, to form solutions having various desired properties and uses. For example, such metal salts have found uses as catalysts, and or as fuel and lubricant additives.

Metallo-organic compositions of this type are also useful as stabilizers for polyvinyl chloride-type plastics.

Another major field of use for this class of compounds is in the area of drying catalysis for paints, varnishes and other coating compositions. This process of drying through the use of metal carboxylates and soaps is discussed generally in Kirk-Othmer, *Concise Encyclopedia of Chemical Technology*, John Wiley & Sons, (1985), pp. 370–371. This article is incorporated herein by reference.

As various organic carboxylic acids have become available in commercial quantities, either from new natural sources, or as synthetic acids or standardized synthetic acid mixtures, the possibility of using these to produce metallic salts or soaps has been motivated, for example, by a lower price; by a relative uniformity of the commercial acids; or by a better color, or at times the non-colored, characteristics of the salt products; by higher solubility of the salt products in various solvents in other components of ultimate products for which the metal salt is to be used; or stability in storage of the metal compositions or of their solutions. Neutral salt or soap compositions contain one mole of a carboxylate group per equivalent of metal present.

SUMMARY OF THE INVENTION

The present invention relates to a process for producing silver salts of at least one organic carboxylic acid, and more particularly, silver carboxylate solutions. The process involves the general steps of:
(A) preparing a mixture of:
  (1) at least one organic carboxylic acid,
  (2) a hydrocarbon solvent, and
  (3) a mineral acid; and
(B) adding a source of silver cation while maintaining the temperature of the resultant mixture between about 60° C. and below the decomposition temperature of the components and product for a period of time sufficient to form the desired silver salt.

DESCRIPTION OF THE PREFERRED EMBODIMENTS

The present invention relates to a method for producing improved silver carboxylates.

The disclosed method comprises generally providing a mixture of: (1) at least one organic carboxylic acid, (2) a hydrocarbon solvent and (3) a mineral acid. To this is added a source of silver cation and the resultant mixture is heated at an effective temperature and for a sufficient amount of time to form the silver carboxylate.

The organic carboxylate acids from which silver carboxylates can be prepared include aliphatic, cycloaliphatic and aromatic mono- and polybasic carboxylic acids. The organic carboxylic acids can be either natural or synthetic, or mixtures thereof. The examples of natural acids, although usually refined, include straight and branched chain carboxylic acids and mixtures such as tall oil acids and cyclic carboxylic acids such as naphthenic acids. A variety of synthetic carboxylic acids, and particularly aliphatic carboxylic acids or mixtures thereof is useful, and these generally contain six or more carbon atoms. The acids contain preferably from 6 to 30 carbon atoms and more preferably from 6 to 15 carbon atoms.

When more than one carboxylic acid is employed, carboxylic acids containing as little as 2 carbon atoms may be employed as one of the acids of the mixture. Examples of useful organic carboxylic acids include acetic acid, propionic acid, butyric acid, isopentanoic acid, hexoic acid, 2-ethyl butyric acid, nonylic acid, decanoic acid, 2-ethylhexoic acid, isooctanoic acid, isononanoic acid, neodecanoic acid, lauric acid, palmitic acid, stearic acid, oleic acid, linoleic acid, naphthenic acid, and commercially available mixtures of two or more carboxylic acids such as naphthenic acid, tall oil acids, rosin acids, etc.

It is preferred that the organic acid be aliphatic (straight chain, branched or alicyclic) and of these those which have a branched chain configuration are preferred.

With regard to the hydrocarbon solvents, any aliphatic or aromatic organic solvent may be used so long as it solvates the silver carboxylate product. For this reason, aromatic solvents are preferred. Aliphatic solvents which may be used include n-hexane, and cyclohexane. Aromatic solvents which may be used include benzene, toluene, xylene, cumene, pseudo cumene and mesitylene. Two solvents which have been found to be particularly useful are pseudocumene (1,2,4-trimethylbenzene) and mesitylene (1,3,5-trimethylbenzene). The preferred of these is pseudocumene.

The mineral acid used may be any of the mineral acids. Nitric acid and sulfurous acid are preferred and of these, nitric acid is particularly preferred. The concentration of the mineral acid in the organic acid/hydrocarbon solvent/mineral acid mixture may be in the range of from about 0.5% to about 20% by weight. A preferred concentration range is from about 1% to about 10% by weight.

The source of silver cation may be any source of free silver cation; for example, silver oxide or silver nitrate. Silver oxide is the preferred as the silver cation source. Optimally, the silver cation source should be dry prior to mixing.

The molar ratio of the silver cation to the organic acid may be as low as about 0.25:1 or as high as about 2:1. While products containing higher or lower ratios can be produced, carboxylates in this general range are those which have been found to have catalytic effectiveness while incorporating an economical amount of precious silver metal.

A more preferred silver cation/organic acid molar ratio range is from about 0.9:1 to about 1.75:1 and a most preferred range is from about 1:1 to about 1.5:1. The most preferred ratio is about 1:1.

The temperature at which the components are mixed to form the silver carboxylate product is important. Because the components and product may decompose at higher temperatures, the mixture must be maintained below its decomposition temperature at all times. The decomposition temperature may vary with the particular reactants, concentrations, etc. of each particular synthesis. It is preferred that the temperature be kept below about 100° C. Below about 60° C., insufficient product is formed, so the range of temperatures for the process is from about 60° C. (preferably 70° C.) to just below the decomposition temperature of the product (typically about 100° C.). A preferred temperature range is from about 85° C. to about 95° C.

In one preferred embodiment, the organic carboxylic acid/hydrocarbon solvent/mineral acid mixture is heated to a temperature below its decomposition temperature prior to the addition of the silver cation source.

In another embodiment, it is preferred that the silver cation source be added in a portionwise fashion while the heated mixture is stirred. This allows much of the silver cation source to dissolve in the reaction mixture during its addition. The temperature of the reaction mixture is then maintained in the preferred range until the product has been formed. The reaction mixture is maintained in the described temperature range until most of the product has been dissolved. This period is typically from about 30 minutes to several hours.

Formation of the product is complete when no more of the reactants will go into solution. After the product has formed, the mixture may be filtered to remove undesirable particulates.

The product is a solution of the silver salt in the solvent. The silver content of the product may be varied over a wide range by varying the amount of solvent introduced into the reaction mixture. Thus the silver concentration can vary from as little as 1% or less up to about 30 or 35%. Typically the silver content will be in the range of about 15-30% by weight. As mentioned above, the silver content also can be varied by varying the ratio of carboxylic acid and silver cation source in the reaction mixture.

The resultant silver carboxylate product is preferably either neutral or slightly basic depending on the presence of excess silver. Products with higher excesses of silver (referred to as "overbased" or "superbased") are feasible but uneconomical due to the high cost of silver.

Silver carboxylates find utility as drying catalysts when incorporated, by use of an organic diluent, into paints, varnishes, inks and other film-forming compositions. They may also be used as catalysts in other applications. One skilled in the additive art may determine the effective and economical amounts for such use.

The invention will be further clarified by a consideration of the following examples which are intended to be purely exemplary of the use of the invention.

Unless otherwise provided, all percentage amounts are expressed as percent by weight.

EXAMPLE 1

A 2.0 liter Erlemmyer flask, heated by a water bath, is charged with 246.0 grams of pseudocumene, 258.0 grams of neodecanoic acid and 5 milliliters of concentrated nitric acid. The mixture is heated to about 90° C., and 186.0 grams of silver oxide are added in a portionwise manner while stirring the mixture. After the addition of the silver oxide is complete, the resultant mixture is maintained at a temperature of about 90° C. for 45 minutes. The product is filtered while still hot. The filtrate is clear or slightly yellow in color. The filtrate is the desired product containing 21% by weight of silver.

EXAMPLE 2

The procedure of Example 1 is repeated except that the neodecanoic acid is replaced by an equivalent amount of naphthenic acid.

EXAMPLE 3

The procedure of Example 1 is repeated except that the silver oxide is replaced by an equivalent amount of silver nitrate.

EXAMPLE 4

The procedure of Example 1 is repeated except that the nitric acid is replaced by an equivalent amount of sulfurous acid.

Other embodiments of the invention will be apparent to one skilled in the art from a consideration of this specification or practice of the invention disclosed herein. It is intended that the specification and examples be considered as exemplary only, with the true scope and spirit of the invention being indicated by the following claims.

I claim:

1. A method of preparing a silver salt of an organic acid consisting essentially of the steps of:
   (A) preparing a mixture of:
      (1) at least one organic carboxylic acid,
      (2) a hydrocarbon solvent,
      (3) a mineral acid; and
   (B) adding silver oxide while maintaining the temperature of the resultant mixture between about 60° C. and below the decomposition temperature of the components and product for a period of time sufficient to form the silver salt.

2. The method of claim 1 wherein said hydrocarbon solvent is an aromatic solvent.

3. The method of claim 1 wherein said organic acid is at least one aliphatic or alicyclic carboxylic acid containing from about 6 to about 30 carbon atoms.

4. The method of claim 3 wherein said organic acid contains from about 6 to about 15 carbon atoms.

5. The method of claim 3 wherein said organic acid is neodecanoic acid.

6. The method of claim 1 wherein the concentration of said mineral acid achieved upon addition of said mineral acid to the mixture in step (A) is in the range of from about 0.5% to about 20% by weight.

7. The method of claim 1 wherein the concentration of said mineral acid achieved upon addition of said mineral acid to the mixture in step (A) is in the range of from about 1% to about 10% by weight.

8. The method of claim 1 wherein the molar ratio of silver cation to said organic acid in the mixture achieved in step (B) is in the range of from about 0.25:1 to about 2:1.

9. The method of claim 1 wherein the molar ratio of silver cation to said organic acid in the mixture achieved in step (B) is in the range of from about 0.9:1 to about 1.75:1.

10. The method of claim 1 wherein the molar ratio of silver cation to said organic acid in the mixture achieved in step (B) is about 1:1.

11. Themethod of claim 1 wherein said mineral acid is nitric or sulfurous acid.

12. The method of claim 1 wherein said mineral acid is nitric acid.

13. The method of claim 1 wherein the mixture in step (B) is maintained at a temperature of from about 85° C. to about 95° C.

14. A method of preparing a silver salt of an organic acid consisting essentially of the steps of:
   (A) preparing a mixture of
      (1) at least one aliphatic or alicyclic carboxylic acid having from about 6 to about 30 carbon atoms,
      (2) a hydrocarbon solvent, and
      (3) nitric acid, and
   (B) adding silver oxide to achieve a molar ratio in the resultant mixture of silver cation to said carboxylic acid of from about 0.25:1 to about 2:1, while maintaining the temperature of said resultant mixture between about 70° C. and below the decomposition temperature of the components and product for a period of time sufficient to form the silver salt.

15. The method of claim 14 wherein said aliphatic or alicyclic carboxylic acid contains from about 6 to about 15 carbon atoms.

16. The method of claim 14 wherein the temperature of said resultant mixture in step (B) is maintained at a temperature of from about 85° C. to about 95° C.

17. The method of claim 14 wherein the concentration of said nitric acid in the mixture of step (A) is in the range of from about 0.5% to about 20% by weight.

18. The method of claim 14 wherein the concentration of said nitric acid in the mixture of step (A) is in the range of from about 1% to about 10% by weight.

19. The method of claim 14 wherein the silver oxide is added portionwise to the mixture of step (A).

20. A method of preparing a silver salt of organic acid consisting essentially of the steps of:
   (A) preparing a mixture of
      (1) at least one alipatic carboxylic acid having from about 6 to about 30 carbon atoms,
      (2) a hydrocarbon solvent, and
      (3) nitric acid, and
   (B) heating the mixture to a temperature not exceeding 100° C.,
   (C) adding silver oxide to achieve a molar ratio in the resultant mixture of the silver cation to said carboxylic acid of from about 1:1 to about 1.5:1 while maintaining the temperature between about 70° C. and below the decomposition temperature of the components and product for a period of time sufficient to form the silver salt.

21. The method according to claim 20 wherein said aliphatic carboxylic acid is neodecanoic acid.

22. The method of claim 21 wherein the temperature maintained in step (C) is in the range of from about 85° C. to about 95° C.

23. The method of claim 20 wherein the addition of the silver oxide in step (C) is effected in a portionwise fashion such that said silver oxide dissolves in the reaction mixture during its addition.

24. The method of claim 20 wherein the silver oxide is substantially dry prior to its addition is step (C).

* * * * *